(12) United States Patent
Liu et al.

(10) Patent No.: US 8,277,616 B2
(45) Date of Patent: Oct. 2, 2012

(54) SURFACE TREATING DEVICE AND SURFACE TREATING METHOD

(75) Inventors: Chi-Hung Liu, Taichung County (TW);
Chun-Hung Lin, Hsinchu (TW);
Chun-Hsien Su, Hsinchu (TW);
Wen-Tung Hsu, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 1178 days.

(21) Appl. No.: 11/892,853

(22) Filed: Aug. 28, 2007

(65) Prior Publication Data
US 2009/0004620 A1 Jan. 1, 2009

(30) Foreign Application Priority Data
Jun. 28, 2007 (TW) .................................. 96123604

(51) Int. Cl.
*B01J 19/08* (2006.01)
(52) U.S. Cl. ..................... 204/164; 433/217.1
(58) Field of Classification Search .................. 204/164; 433/217.1
See application file for complete search history.

(56) References Cited

U.S. PATENT DOCUMENTS

| | | | |
|---|---|---|---|
| 4,210,949 A * | 7/1980 | Masuda | 361/226 |
| 5,597,456 A * | 1/1997 | Maruyama et al. | 204/165 |
| 6,455,014 B1 * | 9/2002 | Hammerstrom et al. | 422/186.04 |
| 6,465,964 B1 * | 10/2002 | Taguchi et al. | 315/111.21 |
| 2006/0156983 A1* | 7/2006 | Penelon et al. | 118/723 E |
| 2007/0029500 A1 | 2/2007 | Coulombe et al. | |

FOREIGN PATENT DOCUMENTS

| | | | |
|---|---|---|---|
| CN | 1064610 A | | 9/1992 |
| JP | 2000-000252 | | 1/2000 |
| KR | 10-0581693 | * | 5/2006 |
| TW | 442271 | | 6/2001 |
| WO | WO-2006112500 | | 10/2006 |

OTHER PUBLICATIONS

M. Teschke et. al.: "High-Speed Photographs of a Dielectric Barrier Atmospheric Pressure Plasma Jet," IEEE Transactions on Plasma Science, vol. 33, No. 2, Apr. 2005, pp. 310 and 311.
Andrew Joiner, "The bleaching of teeth: A review of the literature" Journal of Dentistry, vol. 34, 2006, pp. 412-319.

* cited by examiner

*Primary Examiner* — Kishor Mayekar
(74) *Attorney, Agent, or Firm* — Rabin & Berdo, P.C.

(57) ABSTRACT

A surface treating method for treating a tooth surface and a surface treating device thereof are provided. First, a working gas is filled into a tube. Next, a voltage is provided to the working gas for exciting the working gas into plasma. After that, the plasma is discharged through an opening of the tube for contacting the tooth surface.

11 Claims, 4 Drawing Sheets

SURFACE TREATING DEVICE AND SURFACE TREATING METHOD

This application claims the benefit of Taiwan application Serial No. 96123604, filed Jun. 28, 2007, the subject matter of which is incorporated herein by reference.

BACKGROUND OF THE INVENTION

1. Field of the Invention

The invention relates in general to a surface treating device and a method thereof, and more particularly to a device for treating a tooth surface and a method thereof.

2. Description of the Related Art

As many people consider plastic surgery to be conducive to their work and interpersonal relationship, the need for plastic surgery is ever increasing. Of the various items of plastic surgery, tooth whitening, which enables one to have clean and white teeth and makes one even impressed when smiling, is beloved by people working in the service industries. No matter one's intention is directed towards work or interpersonal relationship, many developed countries such as the United States, European countries and Japan have taken lead in cosmetic dentistry. Nowadays, tooth whitening has become a fashion in many countries. The darkening of one's tooth may be ascribed to overall factors (such as age and personal attributes) or local factors (such as smoking, tea staining, drinking, and food taking). A large portion of local factors result from the pigmentation of organic pigments (C, H, O compounds) on tooth surface. If the organic pigments, which are mainly contained in the food and drinks, are not cleaned timely, pigments will be deposited deep in the teeth and make tooth surface become yellow or darkened.

Tooth whitening methods are divided into several categories. Tooth whitening method may employ bleach alone or employ a light source in addition to the use of bleach. Tooth whitening method may involve more complicated therapy such as porcelain laminate veneer therapy and porcelain crown therapy. According to the porcelain laminate veneer therapy, tooth surface is grounded off the thickness of about two pieces of paper first, and then artificial enamel is coated on the tooth surface to compensate the part of tooth surface grounded off. The porcelain laminate veneer therapy has the advantage of long duration but is too costive. According to the porcelain crown therapy, tooth is grounded into a bar shape on which an alloy crown is planted, and then a porcelain powder with similar color to genuine tooth is fused to the metal crown. The porcelain crown therapy has a wide range of application and a long duration up to 10 years. However, the porcelain crown therapy is the most costive among the current tooth whitening methods, and as a part of tooth or dental pulp is removed, the resulted damage is irreversible.

In the course of tooth whitening, the use of bleach is normally accompanied by the use of a light source to activate the bleach and shorten the course of therapy. Examples of most commonly used light source include halogen light, laser light, light emitting diode and so on. As halogen light source generates more heat than other light sours, it is not suitable to expose the tooth having activity to halogen light for long. The tooth whitening method adopting a laser light or a light emitting diode is called cold-light whitening and produces good tooth-whitening effect. Normally, the ingredients of bleach include oxidizing compounds such as hydrogen peroxide or carbamide peroxide for reacting with the pigments deposited on the tooth surface to result in oxidation. However, most tooth bleaches are for external application only. If bleach is eaten by mistake, damage or side effect may occur. Besides, bleach may stimulate or hurt the soft tissues in the mouth such as the gums. Worse than that, bleach may permeate to the tissue of dental pulp, irritate the sensory nerve and cause allergy. Some bleach may even make the tooth deteriorated or eroded. No matter what method is used, cost, reliability, safety and possible side effects are the focus for improvement.

SUMMARY OF THE INVENTION

The invention is directed to a surface treating device and a method thereof. A tooth surface is treated by plasma generated at a normal pressure. The pigmentation deposited on tooth surface is effectively removed without using any bleach, hence avoiding the side effects associated with the bleach and reducing the cost for whitening the tooth.

According to one aspect of the present invention, a surface treating method for treating a tooth surface is provided. First, a working gas is filled into a tube. Next, a voltage is provided to the working gas for exciting the working gas into plasma at a normal pressure. After that, the plasma is discharged through an opening of the tube for contacting the tooth surface.

According to another aspect of the present invention, a surface treating device including a tube and an electrode set is provided. The tube has a chamber and an opening. The chamber is for receiving a working gas. The electrode set provides a voltage for charging the working gas to generate plasma. The voltage excites the working gas into plasma at a normal pressure, and the plasma is discharged through an opening of the tube for contacting the tooth surface.

According to a further aspect of the present invention, a method for treating a tooth surface by using a surface treating device is provided. The surface treating device includes a tube and an electrode set. The tube has a chamber and an opening. The tooth surface has a colored material. First, a working gas is filled into the chamber. Next, a voltage is provided by the electrode set at a normal pressure for exciting the working gas into plasma. After that, the plasma is discharged through the opening of the tube for removing the pigmentation from the tooth surface.

The invention will become apparent from the following detailed description of the preferred but non-limiting embodiments. The following description is made with reference to the accompanying drawings.

DETAILED DESCRIPTION OF THE INVENTION

In the surface treating method according to the preferred embodiment of the invention, a working gas received in a tube is charged by an electrode set and is excited into plasma at a normal pressure. Afterward, the plasma is discharged through an opening of the tube toward the tooth surface for treating the tooth.

Figure 1:
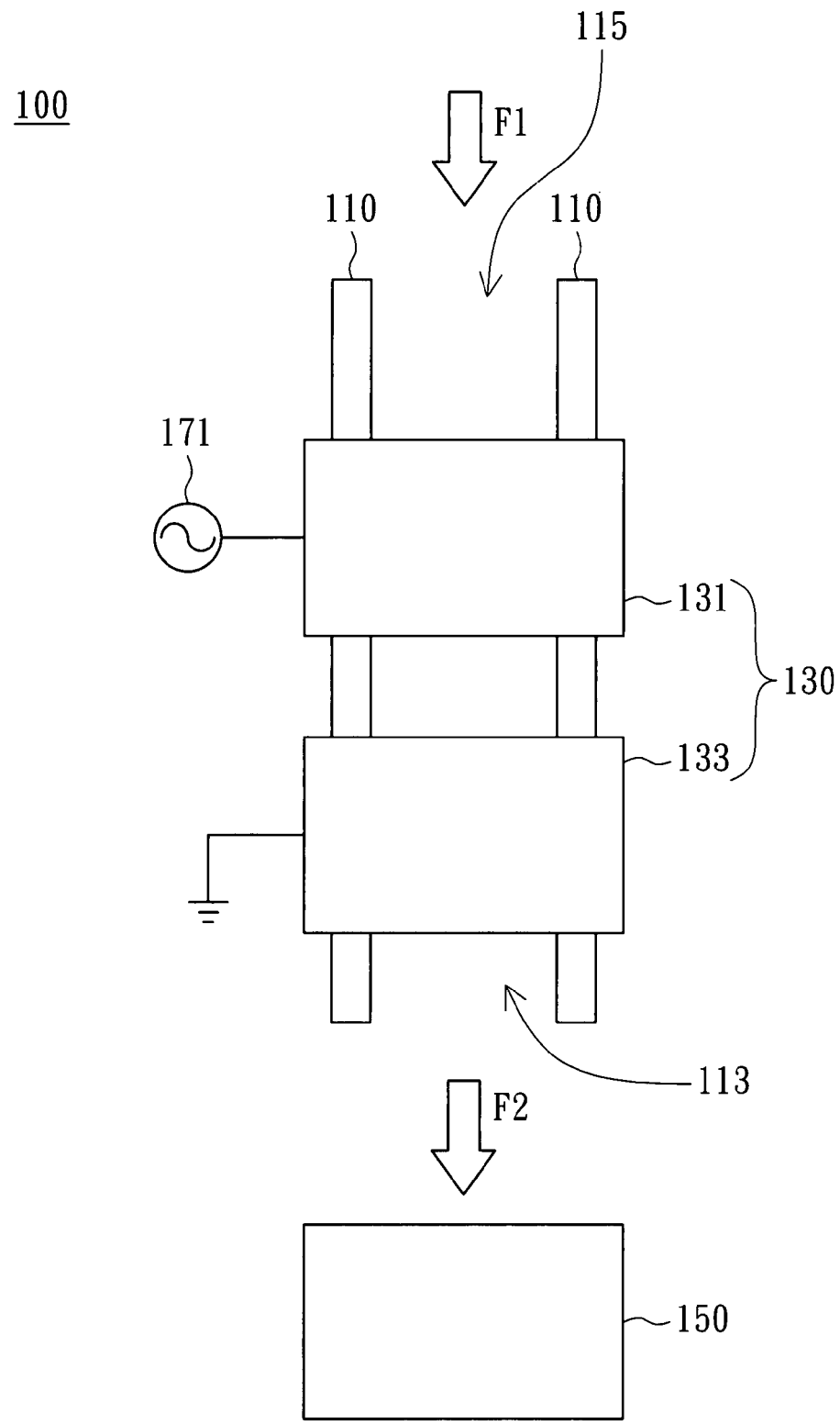
FIG. 1 is a perspective of a surface treating device according to a preferred embodiment of the invention.

Referring to FIG. 1, a perspective of a surface treating device according to a preferred embodiment of the invention is shown. The surface treating device 100 includes a tube 110 and an electrode set 130. The tube 110 has an opening 113 and a chamber 115 used for receiving a working gas. The tube 110 can be disposed either perpendicular or parallel to a horizontal plane. In the present embodiment of the invention, the tube 110 is elaborated by way of perpendicular to the horizontal plane. The electrode set 130 is disposed outside the tube 110 and applies a voltage to the working gas for exciting the working gas into plasma. The plasma is discharged through the opening 113. The to-be-treated tooth surface 150 is disposed at the front end of the opening 113 such that the plasma contacts and treats the tooth surface 150. The chamber 115 is mainly used for providing an environment where the working gas is excited into plasma. The material of the tube 110 is exemplified by a dielectric material such as ceramics or quartz glass.

In the present embodiment of the invention, examples of the working gas include air, argon and helium. The breakdown voltage of helium, ranging between 200~300V, is lower than that of nitrogen and air. Therefore, when helium is used as the working gas, the surface treating device 100 may have a lower working voltage, hence reducing the risk during operation. Moreover, a lower voltage generates a smaller electron multiplication, hence avoiding arc discharge. Further, helium metastables are more stable and can last for several seconds. Because the stationary state energy level for helium is about 20eV, helium can first store a large amount of charge energy, and then release the energy gradually in a long duration. The arc discharging phenomenon generated by massive electrical current within a short period of time can be avoided. Therefore, in the present embodiment of the invention, helium is preferably selected to be the working gas. However, in order to reduce the cost, air or nitrogen may also be selected. In addition to the main working gas, a hydrogen-based (such as water vapor) and/or oxygen-based reacting gas (such as oxygen) may be further added into the main working gas (such as air, argon, nitrogen) to increase the concentration of free radicals generated by the plasma and increase the reaction capability of the plasma.

In the present embodiment of the invention, the plasma is preferably jet plasma. The jet plasma is a low-temperature plasma which can be excited at a normal temperature and a normal pressure. Compared with the other forms of plasma, the concentration of oxygen radicals obtained by the jet plasma is normally 2~4 times in quantity than that of other forms of plasma. For example, the concentration of oxygen radicals obtained from the plasma generated by corona discharge or dielectric barrier discharge (DBD) method is about $10^{12}$ cm$^{-3}$, that obtained from the plasma generated by low-pressure discharge method is about $10^{14}$ cm$^{-3}$, and that obtained from jet plasma is about $10^{16}$ cm$^{-3}$. In addition, the plasma uniformity of jet plasma is better than that of corona discharge. Further, the equipment cost of jet plasma is lower than that of low-pressure plasma. Moreover, the jet plasma not only is applicable to small-area surface treatment, but also obtains high plasma density, ranging from $10^{11}$ cm$^{-3}$ to $10^{12}$ cm$^{-3}$. To sum up, the jet plasma produces better surface treatment effect for the tooth surface 150.

Furthermore, the electrode set 130 includes a first electrode 131 and a second electrode 133. The first electrode 131 is connected to a power supply 171 for providing energy required for exciting the plasma. The second electrode 133 is electrically connected to a grounding surface. The power supply 171 provides a voltage between the first electrode 131 and the second electrode 133. The voltage is applied to the working gas for exciting the working gas into plasma to conduct surface treatment of the tooth surface 150. The power supply 171 can provide continuous current or pulse current. Examples of the power supply include a direct current power supply, an alternate current power supply, or a radio-frequency power supply with a frequency higher than ordinary alternate current. The exemplified frequency of the radio-frequency power supply is 13.56 MHz or integral multiples thereof.

In the present embodiment of the invention, the first electrode 131 and the second electrode 133 can be disposed inside or outside the tube 110 according to actual needs. In the present embodiment of the invention, as indicated in FIG. 1, the first electrode 131 and the second electrode 133 are preferably disposed outside the tube 110. The above disposition not only reduces the electrical field between the electrodes by means of the dielectric material (the material which the chamber 115 is made from), but also reduces the number of electrons flowing to the positive electrode and prevents arc discharge. In practical application, the electrode can be disposed in various manners. For example, the first electrode 131 can be disposed outside the tube 110 and surrounds the tube 110. The first electrode 131 is disposed at one end of the tube 110 corresponding to the opening 113. Besides that, the first electrode 131 can also be disposed outside the tube 110 in the form of a spiral coil. Furthermore, the first electrode 131 and the second electrode 133 can be disposed at two opposite sides outside the tube 110 as an electrode plate respectively. On the other hand, with appropriate design of the electrode and appropriate selection of the power supply 171, the temperature of the plasma can be controlled to meet the requirement for treating the tooth surface 150. For example, the plasma temperature in treating the denture can be increased such that the pigmentation deposited on the tooth surface is removed effectively; or the plasma temperature is maintained approximate to body temperature to ease the discomfort of the patient and to avoid burns during the whitening process.

Figure 2:
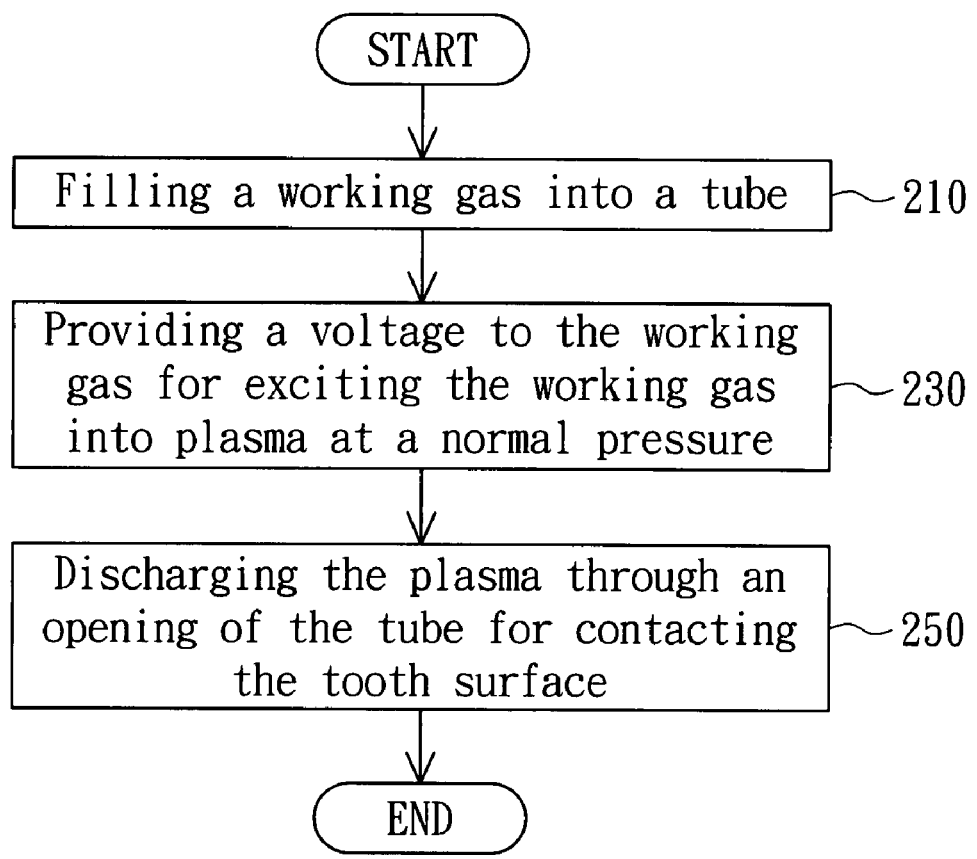
FIG. 2 is a flowchart of a surface treating method according to a preferred embodiment of the invention.

Also, the surface treating method of the preferred embodiment of the invention is applicable to the surface treating device disclosed in the above. Referring to FIG. 1 and FIG. 2 at the same time, FIG. 2 is a flowchart of a surface treating method according to a preferred embodiment of the invention.

The surface treating method of the present embodiment of the invention starts from step 210. As indicated in step 210, a working gas is filled into the tube 110 along a direction F1. If air is chosen as the working gas, it can be provided by air-supplying equipment such as air compressor or simply by sucking the filtered air. For generating plasma free of impurities, an inert gas can be chosen as the working gas. Furthermore, the inert gas is sotred in a clean gas steel cylinder to avoid pollution. Apart from the main reaction gas, an additional reaction gas can be filled to increase the reaction capability of the excited plasma.

Next, the method proceeds to step 230, a voltage is provided to the working gas for exciting the working gas into plasma at a normal pressure. In step 230, the voltage is provided to the working gas by the electrode set 130; the first electrode 131 is connected to the power supply 171 for providing energy and the second electrode 133 is electrically connected to the grounding surface, so as to excite the working gas inside the tube 110 into jet plasma. Besides, in step 230, plasma is excited at a normal temperature and thus lowering the involved risk. The generated plasma having a temperature close to room temperature is suitable for treating the tooth surface 150 of genuine tooth having activity and easing the discomfort of the patient during the whitening process.

After that, as indicated in step 250, the plasma is discharged through the opening 113 of the tube 110 for contacting the tooth surface 150. In the present embodiment of the invention, the to-be-treated tooth surface 150 is disposed at the opening 113 of the tube 110, such that the excited jet plasma is jetted to the tooth surface 150 from the opening 113 along a direction F2 for treating the tooth surface. The surface treating device of the present embodiment of the invention can be designed as a portable device, and that the opening 113 of the tube 110 can be placed into the patient's mouth when treating the tooth surface 150. Further, the surface treating device can also be designed as a fixed device, such that the denture is fixed at the front end of the opening 113 for automatically or manually whitening or cleaning the surface of the denture.

Figure 3:
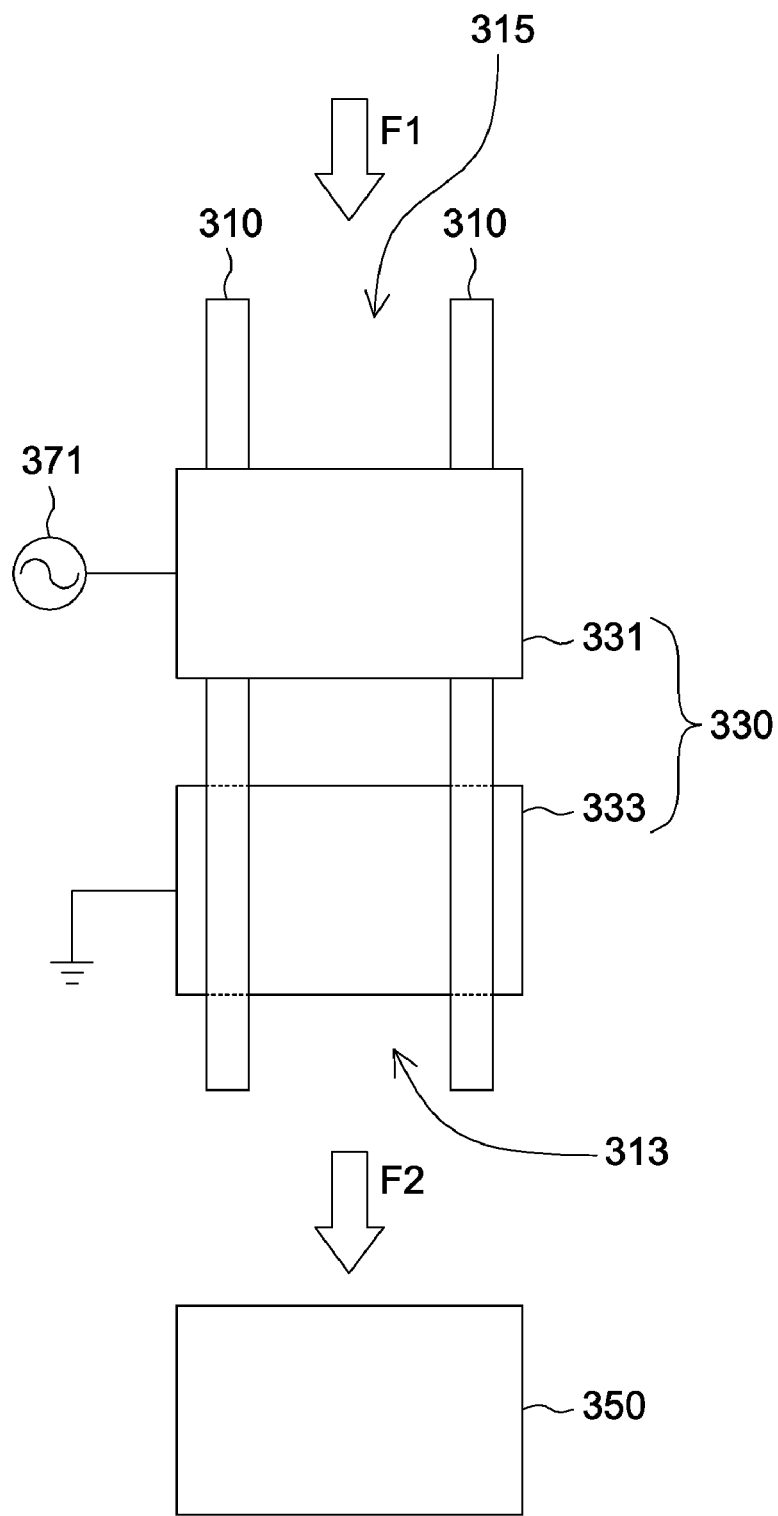
FIG. 3 is a perspective of a surface treating device according to another embodiment of the invention.
Figure 4:
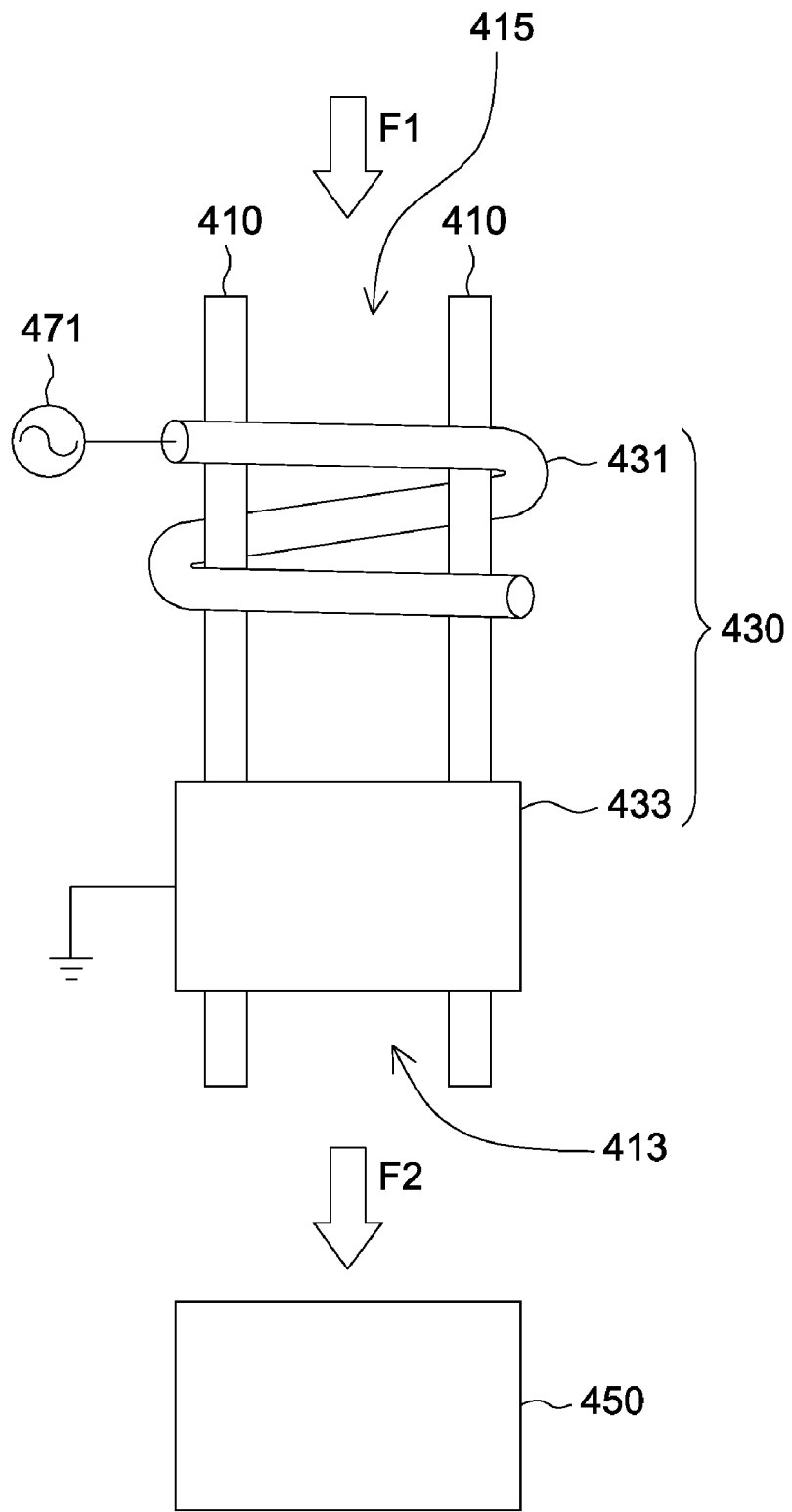
FIG. 4 is a perspective of a surface treating device according to still another embodiment of the invention.

FIG. 3 is a perspective of a surface treating device according to another embodiment of the invention. As shown in FIG. 3, a surface treating device 300 includes a tube 310 and an electrode set 330. The tube 310 has an opening 313 and a chamber 315 used for receiving a working gas. The electrode set 330 has a first electrode 331 and the second electrode 333. The first electrode 331 is connected to a power supply 371 for providing energy required for exciting the plasma. The first electrode 331 and the second electrode 333 are electrode boards and are respectively disposed at two opposite sides outside the tube 310 in parallel. The opening 313 of the tube 310 can be placed into the patient's mouth when treating the tooth surface 350. FIG. 4 is a perspective of a surface treating device according to still another embodiment of the invention. As shown in FIG. 4, a surface treating device 400 includes a tube 410 and an electrode set 430. The tube 410 has an opening 413 and a chamber 415 used for receiving a working gas. The electrode set 430 has a first electrode 431 and the second electrode 433. The first electrode 431 is connected to a power supply 471 for providing energy required for exciting the plasma. The first electrode 431 is disposed outside the tube 410 in the form of a coil. The opening 413 of the tube 410 can be placed into the patient's mouth when treating the tooth surface 450.

According to the surface treating device and the method thereof disclosed in the above preferred embodiment of the invention, a jet plasma is generated by a surface treating device at a normal pressure for removing the pigmentation deposited on the tooth surface without using any bleach. The surface treating device and method thereof provided in the present embodiment of the invention have the following advantages:

1. The design of the present embodiment of the invention reduces the occurrence of arc discharge and avoids the electrode from being penetrated, thus not only reducing electrode damage but also prolonging the lifespan of the electrode and the equipment.

2. The jet plasma used in the present embodiment of the invention having the features of high density and high uniformity is also applicable to the whitening and the cleaning of a denture.

3. The jet plasma used in the present embodiment of the invention is a low-temperature plasma which generates less heat than arc and torch plasma does, hence is applicable to the whitening and cleaning of the surface of a genuine tooth.

4. The plasma used in the present embodiment of the invention is excited at a normal pressure without resorting to any vacuum system, hence reducing equipment cost and increasing safety in operation. The surface treating device and method thereof provided in the present embodiment of the invention can be integrated into a continuous treatment process. For example, by incorporating an ultrasonic scaler with the surface treating device of the present embodiment of the invention, the denture is directly whitened after cleaning by the ultrasonic scaler, so that pigmentation is removed from the tooth surface more effectively.

5. The surface treating device and method thereof provided in the present embodiment of the invention can take effect in a single process step without bleach. As the concentration of the generated oxygen radicals is as high as $10^{16}$ cm$^{-3}$, the procedures and period of treatment can be largely simplified and shortened. Also, the surface treatment of the present embodiment is free of the side effects arisen from bleach, and is more acceptable to the users.

6. The surface treating device and method thereof provided in the present embodiment of the invention use air or nitrogen as the working gas, not only reducing cost but also avoiding environmental issues.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A surface treating method for treating a tooth surface, the tooth surface having a colored material, the method comprising:
    filling a working gas into a tube;
    providing a voltage to an electrode set for exciting the working gas into plasma at a normal pressure, the electrode set comprising a first electrode and a second electrode and the electrode set being disposed outside the tube; and
    discharging the plasma through an opening of the tube for contacting the tooth surface to remove the colored material, wherein the plasma forms a jet plasma, the jet plasma generates oxygen radicals with a concentration of $10^{16}$cm$^{-3}$.

2. The surface treating method according to claim 1, wherein the step of providing the voltage is performed at a normal temperature.

3. The surface treating method according to claim 1, wherein the step of providing the voltage further comprises:
    electrically connecting the first electrode to a power supply; and
    electrically connecting the second electrode to an external grounding surface, wherein the voltage is provided between the first electrode and the second electrode.

4. The surface treating method according to claim 3, wherein the first electrode surrounds the outside of the tube and is disposed at one end of the tube corresponding to the opening.

5. The surface treating method according to claim 3, wherein the first electrode is in the form of a coil.

6. The surface treating method according to claim 3, wherein the first electrode and the second electrode are an electrode board respectively and are disposed at two opposite sides outside the tube in parallel.

7. The surface treating method according to claim 1, wherein before the step of discharging the plasma, the method further comprises:
    disposing the tooth surface at the opening.

8. The surface treating method according to claim 1, wherein the working gas comprises argon or nitrogen.

9. The surface treating method according to claim 8, wherein the working gas further comprises hydrogen-based and oxygen-based gas.

10. The surface treating method according to claim 1, wherein the working gas comprises air.

11. The surface treating method according to claim 10, wherein the working gas further comprises hydrogen-based and oxygen-based gas.

* * * * *